(12) United States Patent
Yamazaki et al.

(10) Patent No.: US 9,682,942 B2
(45) Date of Patent: Jun. 20, 2017

(54) FORM OF PYRIMIDINE COMPOUND HAVING DIBENZYLAMINE STRUCTURE

(71) Applicant: KOWA COMPANY, LTD., Aichi (JP)

(72) Inventors: Koichi Yamazaki, Tokyo (JP); Kennosuke Matsuda, Tokyo (JP); Taichi Kusakabe, Chiba (JP); Tadaaki Ohgiya, Saitama (JP); Kimiyuki Shibuya, Saitama (JP)

(73) Assignee: KOWA COMPANY, LTD., Aichi (JP)

( * ) Notice: Subject to any disclaimer, the term of this patent is extended or adjusted under 35 U.S.C. 154(b) by 0 days.

(21) Appl. No.: 14/784,147

(22) PCT Filed: May 30, 2014

(86) PCT No.: PCT/JP2014/064372
§ 371 (c)(1),
(2) Date: Oct. 13, 2015

(87) PCT Pub. No.: WO2014/192903
PCT Pub. Date: Dec. 4, 2014

(65) Prior Publication Data
US 2016/0031827 A1    Feb. 4, 2016

(30) Foreign Application Priority Data

May 31, 2013   (JP) ................................ 2013-115189

(51) Int. Cl.
*A01N 43/54* (2006.01)
*A61K 31/505* (2006.01)
*C07D 239/47* (2006.01)

(52) U.S. Cl.
CPC ........ *C07D 239/47* (2013.01); *C07B 2200/13* (2013.01)

(58) Field of Classification Search
CPC .......................... C07B 2200/13; C07D 239/47
See application file for complete search history.

(56) References Cited

U.S. PATENT DOCUMENTS

| | | | |
|---|---|---|---|
| 5,883,092 A | 3/1999 | Hirata et al. | |
| 8,906,895 B2 * | 12/2014 | Ohgiya ................ | C07D 239/47 514/183 |
| 2005/0059810 A1 | 3/2005 | Maeda et al. | |
| 2008/0146620 A1 | 6/2008 | Maeda et al. | |
| 2009/0082352 A1 | 3/2009 | Ohgiya et al. | |
| 2013/0225618 A1 | 8/2013 | Shibuya et al. | |
| 2013/0225814 A1 | 8/2013 | Ohgiya et al. | |

FOREIGN PATENT DOCUMENTS

| | | | |
|---|---|---|---|
| CN | 1196051 A | 10/1998 | |
| CN | 101679309 A | 3/2010 | |
| CN | 102933559 A | 2/2013 | |
| EP | 2 578 574 A1 | 4/2013 | |
| JP | 2004-323504 A | 11/2004 | |
| JP | 2013-136572 A | 7/2013 | |
| WO | 2008/129951 A1 | 10/2008 | |
| WO | 2011/152508 A1 | 12/2011 | |
| WO | WO 2011152508 A1 * | 12/2011 | ........... C07D 239/47 |
| WO | 2012/046681 A1 | 4/2012 | |
| WO | 2013/081087 A1 | 6/2013 | |

OTHER PUBLICATIONS

Mino R. Caira, "Crystalline Polymorphism of Organic Compounds", Topics in Current Chemistry, vol. 198, 1998, pp. 163-208.
European Search report issued with respect to Application No. 14804509.9, mail date is Oct. 4, 2016.
Japanese Office Action issued with respect to Application No. 2014-113680, mail date is Aug. 2, 2016.
Chinese Office Action issued with respect to Application No. 201480030617.6, mail date is Jul. 18, 2016.
Bavin et al., "Polymorphism in Process Development, Chemistry & Industry", Aug. 23, 1989, pp. 527-529, (16).
Byrn et al., "Pharmaceutical Solids: a Strategic Approach to Regulatory Considerations", Pharmaceutical Research, vol. 12, No. 7, 1995, pp. 945-954.
International Search Report issued with respect to application No. PCT/JP2014/064372, mail date Jul. 15, 2014.
International Preliminary Report on Patentability issued with respect to application No. PCT/JP2014/064372, mail date Dec. 1, 2015.

* cited by examiner

*Primary Examiner* — Jean Cornet
(74) *Attorney, Agent, or Firm* — Greenblum & Bernstein, P.L.C.

(57) ABSTRACT

It is an object of the present invention to provide a novel form of (S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid, which is useful for preventing and/or treating diseases such as dyslipidemia. (S)-trans-{4-[({2-[({1-[3,5-bis(Trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid hydrochloride.

4 Claims, 2 Drawing Sheets

FORM OF PYRIMIDINE COMPOUND HAVING DIBENZYLAMINE STRUCTURE

TECHNICAL FIELD

The present invention relates to a novel form of (S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid, which is a pyrimidine compound having a dibenzylamine structure useful for preventing and/or treating diseases such as dyslipidemia.

BACKGROUND ART

It has been known that (S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid (hereinafter also referred to as a "pyrimidine compound (1)" in the present description) represented by the following formula (1):

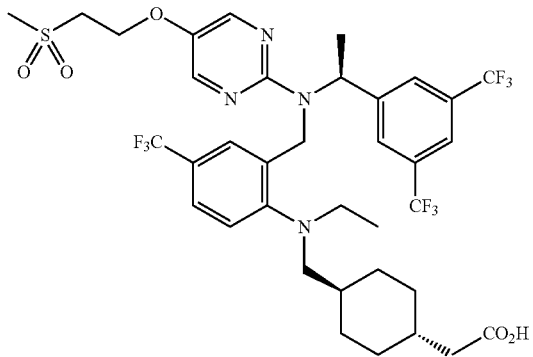

(1)

has an action to inhibit a cholesteryl ester transfer protein (CETP), an action to reduce the amount of proprotein convertase subtilisin/kexin 9 (PCSK9) protein and the like, and that this compound is useful for preventing or treating diseases such as dyslipidemia (Patent Literatures 1, 2, and 3).

With regard to the pyrimidine compound (1), it has been disclosed so far that a racemate thereof was obtained in the form of a light yellow oil in Example 45 of Patent Literature 1. In addition, it has also been disclosed in Example 1 of Patent Literature 2 and Production Example 2 of Patent Literature 3 that the pyrimidine compound (1) was obtained in the form of a white amorphous substance.

However, a crystal of the pyrimidine compound (1) has not yet been reported so far.

In general, if a means for crystallizing a low-molecular weight compound available as an active ingredient of pharmaceutical product were established, the purity thereof could be improved by recrystallization. Thus, a high-purity pharmaceutical product can be provided. Moreover, when compared with forms having poor crystallinity, such as an amorphous substance and an amorphous solid, a crystal has excellent homogeneity and less likely to cause unevenness in solubility and the like. Hence, it becomes possible to provide a homogeneous pharmaceutical product from such a crystal. Furthermore, since the crystal is generally a solid and is easily handled, it is advantageous for production of a pharmaceutical preparation.

Considering the aforementioned advantages, in general, it is desired to develop a crystal form from a low-molecular-weight compound available as an active ingredient of pharmaceutical product. However, it is extremely unlikely to predict the formation of a crystal from a compound, and thus, under the current circumstances, the possibility of formation of a crystal, conditions for crystal formation, etc. are totally unknown until they are actually examined.

CITATION LIST

Patent Literature

[Patent Literature 1] WO 2008/129951
[Patent Literature 2] WO 2011/152508
[Patent Literature 3] WO 2012/046681

SUMMARY OF INVENTION

Technical Problem

It is an object of the present invention to provide a novel form of the pyrimidine compound (1) useful for preventing and/or treating diseases such as dyslipidemia.

Solution to Problem

In order to achieve the aforementioned object, the present inventors have first conducted intensive studies regarding crystallization of a free form of the pyrimidine compound (1). However, it has been difficult to crystallize the pyrimidine compound (1), which is in the state of a free form, and although the inventors have studied it under various conditions, they could not obtain a crystal.

Hence, the present inventors have converted the pyrimidine compound (1) to various salts, and have then conducted more intensive studies regarding crystallization of the salts. As a result, the inventors have found that a sulfate, an arginine salt and the like of the pyrimidine compound (1), and also a hydrobromate which is one of hydrohalogenic acid salts could not be crystallized, but that when the pyrimidine compound (1) was converted to a hydrochloride which is also one of hydrohalogenic acid salts, a crystal having excellent heat stability could be specifically obtained, and using the obtained crystal, a stable pharmaceutical composition could be provided, thereby completing the present invention.

Specifically, the present invention relates to, for example, the following inventions.

[1] A hydrochloride of (S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid.

[2] The hydrochloride according to [1], which is a monohydrochloride.

[3] A crystal of (S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid hydrochloride.

[4] The crystal according to [3], which is a monohydrochloride.

[5] The crystal according to [3] or [4], wherein the powder X-ray diffraction pattern obtained by irradiation with copper Kα X rays has a peak(s) at one or more diffraction angles (2θ) selected from the group consisting of around 14.0±0.2°, around 18.3±0.2°, around 20.1±0.2°, around 20.5±0.2°, around 21.3±0.2°, around 21.8±0.2°, around 23.3±0.2°, and around 24.0±0.2°.

[6] The crystal according to [3] or [4], wherein the powder X-ray diffraction pattern obtained by irradiation with copper Kα X rays has a peak at a diffraction angle (2θ) around 20.5±0.2°.

[7] The crystal according to [3] or [4], wherein the powder X-ray diffraction pattern obtained by irradiation with copper Kα X rays has peaks at diffraction angles (2θ) around 18.3±0.2° and around 20.5±0.2°.

[8] The crystal according to [3] or [4], wherein the powder X-ray diffraction pattern obtained by irradiation with copper Kα X rays has peaks at diffraction angles (2θ) around 14.0±0.2°, around 18.3±0.2°, around 20.1±0.2°, around 20.5±0.2°, around 21.3±0.2°, around 21.8±0.2°, around 23.3±0.2°, and around 24.0±0.2°.

[9] The crystal according to [3] or [4], wherein the powder X-ray diffraction pattern obtained by irradiation with copper Kα X rays is substantially identical to that shown in FIG. 1.

[10] The crystal according to any of [3] to [9], which has an endothermic peak around 162±5.0° C. in differential thermal analysis (DTA).

[11] The crystal according to any of [3] to [9], wherein the results of thermal analysis measurements (differential thermal analysis (DTA) and thermogravimetry (TG)) are substantially identical to those shown in FIG. 2.

[12] A pharmaceutical composition comprising the compound according to any of [1] to [11] above.

[13] A pharmaceutical composition comprising the compound according to any of [1] to [11] above and a pharmaceutically acceptable carrier.

[14] A method for producing a pharmaceutical composition, comprising a step of mixing the compound according to any of [1] to [11] above with a pharmaceutically acceptable carrier.

[15] Use of the compound according to any of [1] to [11] above for production of a pharmaceutical composition.

[16] Use of the compound according to any of [1] to [11] above as a raw material for production of a pharmaceutical composition.

[17] The compound according to any of [1] to [11] above for use in production of a pharmaceutical composition.

[18] The compound according to any of [1] to [11] above used as a raw material for production of a pharmaceutical composition.

Advantageous Effects of Invention

The hydrochloride of the pyrimidine compound (1) according to the present invention can be used as a raw material for formation of a crystal of the pyrimidine compound (1), which is difficult to be crystallized.

Moreover, the crystal of the pyrimidine compound (1) hydrochloride has high heat stability and is useful for production of a high-quality pharmaceutical product.

Figure 1:
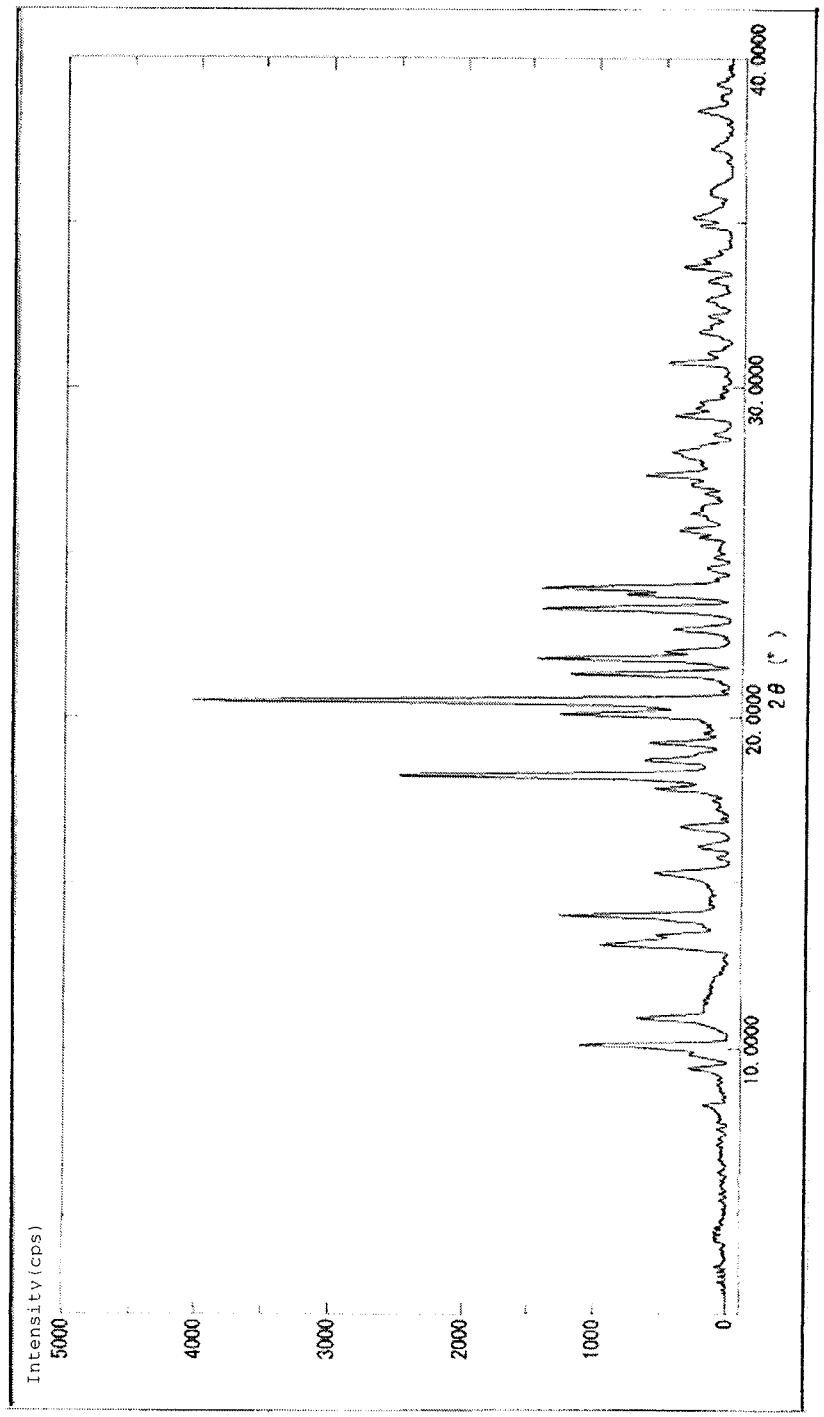
FIG. 1 is a view showing a powder X-ray diffraction pattern of the crystal of the pyrimidine compound (1) hydrochloride obtained in 1-3 of Example 1.

DESCRIPTION OF EMBODIMENTS (S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid (pyrimidine compound (1)) is represented by the above formula (1), and a free form of this compound is disclosed, for example, in Patent Literature 2 and Patent Literature 3. The descriptions of these literatures are cited herein by reference in their entirety.

With regard to the hydrochloride of the pyrimidine compound (1), the number of molecules of hydrogen chloride is not particularly limited, and it may be any one of a monohydrochloride, a dihydrochloride, a trihydrochloride and a tetrahydrochloride, or it may also be a mixture thereof. A monohydrochloride is preferable because the compound can be obtained in the form of a stable acid-added salt.

In the present invention, the hydrochloride of the pyrimidine compound (1) is preferably
(S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid monohydrochloride
represented by the following formula (2):

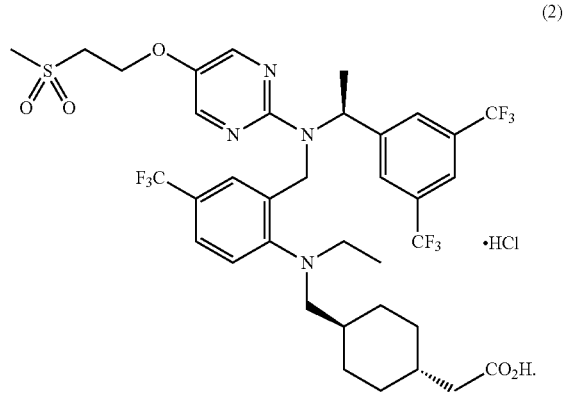 [SMILES: CCN(C[C@H]1CC[C@H](CC(=O)O)CC1)c1ccc(C(F)(F)F)cc1CN(c1ncc(OCCS(C)(=O)=O)cn1)[C@@H](C)c1cc(C(F)(F)F)cc(C(F)(F)F)c1 ; Cl]

The specific crystal form of the crystal of the pyrimidine compound (1) hydrochloride is not particularly limited. It may be any one of different crystal forms, or it may also be a mixture thereof. Further, it may also be a mixture of the crystal of the pyrimidine compound (1) hydrochloride with the amorphous substance of the pyrimidine compound (1) hydrochloride.

Whether or not the pyrimidine compound (1) hydrochloride is a crystal can be confirmed by known methods that are used to determine crystallinity, such as X-ray diffraction measurement (specifically, powder X-ray diffraction measurement, etc.), thermal analysis measurements (specifically, a differential thermal analysis method (DTA), a differential scanning calorimetry (DSC), etc.), confirmation of polarization (specifically, observation under a polarization microscope, etc.), and a solid NMR measurement. For example, a certain solid-state pyrimidine compound (1) hydrochloride is subjected to a powder X-ray diffraction measurement involving irradiation with copper Kα X rays. When a clear peak is observed, it can be confirmed that the pyrimidine compound (1) hydrochloride is a crystal. It is to be noted that such methods of determining crystallinity (a powder X-ray diffraction measurement method, a thermal analysis method, etc.) can be carried out with reference to the descriptions of Japanese Pharmacopoeia, US Pharmacopeia, European Pharmacopoeia, etc.

Moreover, confirmation of the crystal may be carried out in the coexistence of other components. For example, in the case of a solid pharmaceutical composition (a tablet, a capsule, a granule, a powder, etc.) comprising the hydrochloride of the pyrimidine compound (1) and a pharmaceutically acceptable carrier, the solid pharmaceutical composition is crushed as necessary, and is then subjected to an X-ray diffraction measurement. When a peak derived from the hydrochloride of the pyrimidine compound (1) is observed, the hydrochloride of the pyrimidine compound (1) can be confirmed to be a crystal.

In the present invention, the crystal of the pyrimidine compound (1) hydrochloride is preferably a crystal, wherein the powder X-ray diffraction pattern obtained by irradiation with copper Kα X rays has a peak(s) at one or more diffraction angles (2θ) selected from the group consisting of, at least, around 14.0±0.2°, around 18.3±0.2°, around 20.1±0.2°, around 20.5±0.2°, around 21.3±0.2°, around 21.8±0.2°, around 23.3±0.2°, and around 24.0±0.2°; more preferably a crystal, wherein the powder X-ray diffraction pattern has a peak at least at a diffraction angle (2θ) around 20.5±0.2°; even more preferably a crystal, wherein the powder X-ray diffraction pattern has peaks at least at diffraction angles (2θ) around 18.3±0.2° and around 20.5±0.2°; further preferably a crystal, wherein the powder X-ray diffraction pattern has peaks at least at diffraction angles (2θ) around 14.0±0.2°, around 18.3±0.2°, around 20.1±0.2°, around 20.5±0.2°, around 21.3±0.2°, around 21.8±0.2°, around 23.3±0.2°, and around 24.0±0.2°; and particularly preferably a crystal substantially identical to that shown in FIG. 1.

Figure 2:
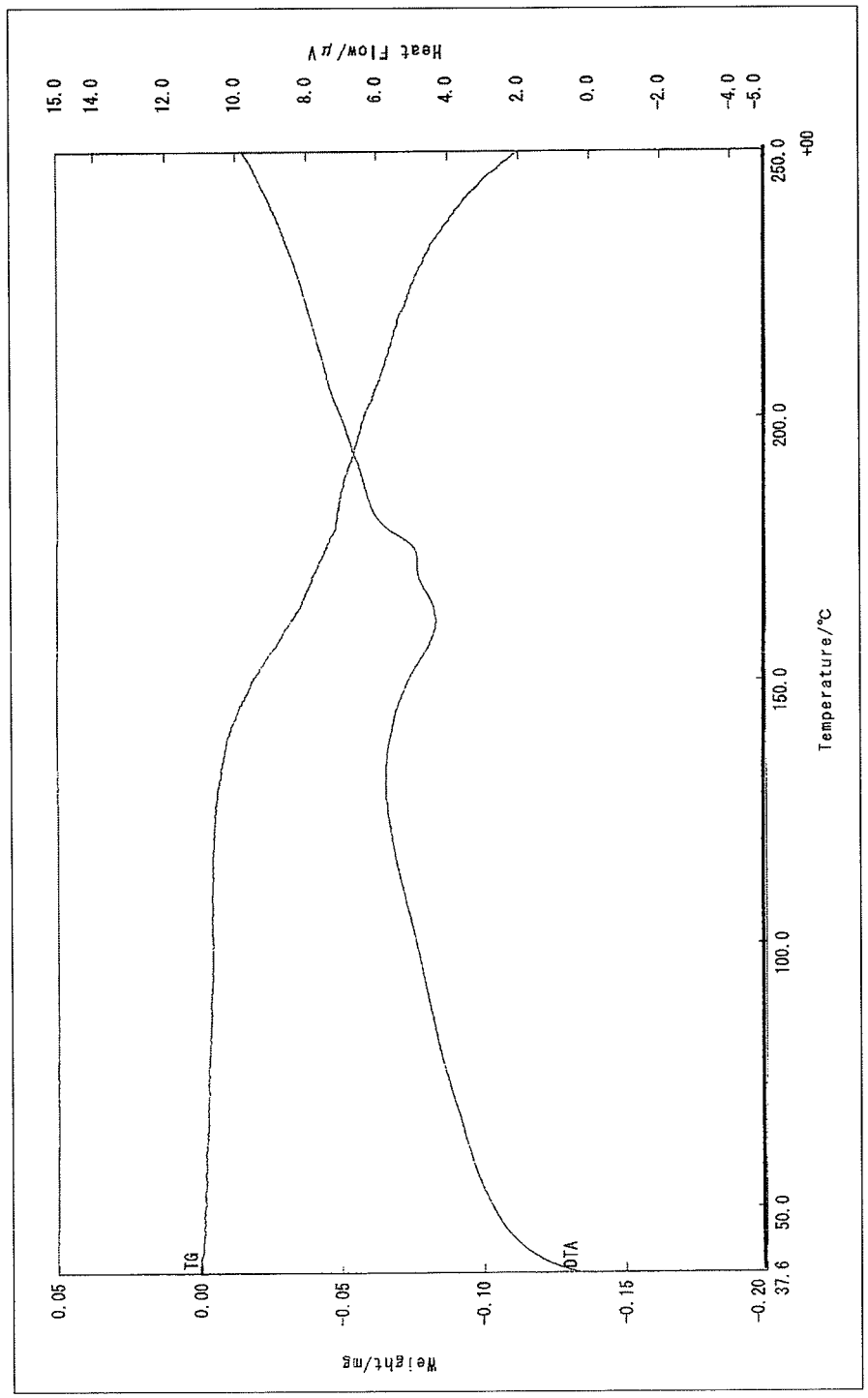
FIG. 2 is a view showing the data of thermal analysis measurements (TG-DTA measurements) of the crystal of the pyrimidine compound (1) hydrochloride obtained in 1-3 of Example 1.

Moreover, from another viewpoint, in the present invention, the crystal of the pyrimidine compound (1) hydrochloride is preferably a crystal having an endothermic peak around approximately 162±5° C. in differential thermal analysis (DTA), and is more preferably a crystal, the results of thermal analysis measurements (differential thermal analysis (DTA) and thermogravimetry (TG)) of which are substantially identical to those shown in FIG. 2.

It is to be noted that the hydrochloride of the pyrimidine compound (1) of the present invention and the crystal thereof may be a solvate such as a hydrate, or a non-solvate such as an anhydride. The hydrochloride of the pyrimidine compound (1) of the present invention and the crystal thereof are preferably anhydrides.

In the present invention, the hydrochloride of the pyrimidine compound (1) and the crystal thereof can be produced, for example, by the following steps, respectively:
(Step 1) a step of forming a hydrochloride from a free form of the pyrimidine compound (1); and
(Step 2) a step of forming a crystal from the hydrochloride of the pyrimidine compound (1).

Hereinafter, individual steps will be described in detail, separately. However, the methods for producing the hydrochloride of the pyrimidine compound (1) of the present invention and the crystal thereof are not limited to the method described below.

<Step 1: Formation of Hydrochloride from Free Form of Pyrimidine Compound (1)>

The present step is a step of forming a hydrochloride by allowing a pyrimidine compound (1) to coexist with hydrogen chloride in the presence of a solvent. Specifically, the present step is a step of dissolving a free form of the pyrimidine compound (1) in a solvent and supplying hydrogen chloride to the solvent to form a salt.

In the present step, the free form of the pyrimidine compound (1) used as a starting material can be produced, for example, according to the method described in Patent Literature 2.

The present step is carried out in the presence of a solvent. The solvent used herein is not particularly limited, as long as it is not involved in formation of a hydrochloride. Examples of the solvent include: aromatic hydrocarbons such as benzene, toluene, xylene, mesitylene, chlorobenzene, 1,2-dichlorobenzene, and nitrobenzene; ethers such as diethyl ether, diisopropyl ether, tert-butyl methyl ether, and 1,4-dioxane; acetic acid esters such as ethyl acetate, n-propyl acetate, and isopropyl acetate; ketones such as acetone, 2-butanone, and 3-pentanone; aliphatic hydrocarbons such as n-pentane, n-hexane, n-heptane, cyclohexane, n-octane, and n-decane; amides such as N,N-dimethylformamide and N,N-dimethylacetamide; and sulfoxides such as dimethyl sulfoxide. These solvents can be used singly or in combination of two or more solvents. When two or more solvents are used, the solvents may be mixed, and the pyrimidine compound (1) may be then dissolved in the mixed solvent. Alternatively, the pyrimidine compound (1) may be dissolved in a solvent, and the remaining solvents may be then added to the obtained mixture.

As such a solvent, one or more selected from the group consisting of diisopropyl ether, tert-butyl methyl ether, 1,4-dioxane, n-hexane, n-heptane, ethyl acetate and isopropyl acetate are preferable; one or more selected from the group consisting of diisopropyl ether, tert-butyl methyl ether, 1,4-dioxane and isopropyl acetate are more preferable; and tert-butyl methyl ether or isopropyl acetate is particularly preferable.

The amount of such a solvent is not particularly limited. The solvent may be used in an amount 1 to 20 times (V/W), and preferably 5 to 15 times (V/W), at a volume ratio with respect to the weight of the free form of the pyrimidine compound (1).

The supply source of hydrogen chloride is not particularly limited. Hydrogen chloride gas may be directly blown into the solution. Otherwise, available concentrated hydrochloric acid, a 4 M HCl/ethyl acetate solution, a 4 M HCl/1,4-dioxane solution, etc. can be used.

The amount of hydrogen chloride is not particularly limited, and the hydrogen chloride is used in an amount of preferably 1 to 5 molar equivalents, and particularly preferably 1 to 4 molar equivalents, with respect to the free form of the pyrimidine compound (1).

The temperature applied upon formation of a salt is not particularly limited. It is in the range of generally −50° C. to 150° C., preferably −20° C. to 80° C., and more preferably −10° C. to 40° C. The time required for formation of a salt is not particularly limited. It is generally from 5 minutes to 48 hours, preferably from 30 minutes to 24 hours, and more preferably from 30 minutes to 3 hours.

The generated hydrochloride of the pyrimidine compound (1) can be isolated. In this case, the salt precipitated as a solid may be isolated by a method which is commonly applied in the present technical field, such as filtration, and further, the isolated salt may be dried, as necessary, by a method commonly applied in the present technical field. The drying means is not particularly limited, and examples of the drying means include heating and/or drying under reduced pressure conditions. The drying temperature is preferably 50° C. or lower, and more preferably from 40° C. to 50° C. The drying time is preferably from 1 to 24 hours, and more preferably from 6 to 12 hours.

<Step 2: Formation of Crystal from Hydrochloride of Pyrimidine Compound (1)>

The present step is a step of crystallizing, in the presence of a solvent, the hydrochloride of the pyrimidine compound (1) (e.g., an amorphous substance) obtained in Step 1. Specifically, the present step is a step of adding the hydrochloride of the pyrimidine compound (1) obtained in Step 1 to a solvent, then, as necessary, dissolving the hydrochloride in the solvent by heating or the like, and then crystallizing by cooling or the like.

The present step is carried out in the presence of a solvent. Examples of the solvent include a mixed solution of 2-propanol and heptane, and a mixed solution of methyl ethyl ketone and heptane. Of these, a mixed solution of 2-propanol and heptane is preferable. The mixing ratio of solvents is not particularly limited. Heptane may be used in an amount 0.1 to 2 times (V/V), and preferably 0.2 to 1 time (V/V), at a volume ratio with respect to the volume of 2-propanol or methyl ethyl ketone.

When the hydrochloride of the pyrimidine compound (1) is dissolved in the solvents, after the solvents have previously been mixed with each other, the hydrochloride of the pyrimidine compound (1) may be dissolved in the mixed solvent. Otherwise, it is preferable that the hydrochloride of the pyrimidine compound (1) is dissolved in 2-propanol or methyl ethyl ketone, and that heptane is then added to the obtained solution.

The amounts of the solvents are not particularly limited. With regard to the total amount of the mixed solvent, the mixed solvent may be used in an amount 1 to 20 times (V/W), and preferably 5 to 10 times (V/W), at a volume ratio with respect to the weight of the hydrochloride of the pyrimidine compound (1).

The temperature applied when the hydrochloride of the pyrimidine compound (1) is dissolved in a solvent is not particularly limited. It may be generally in the range of 40° C. to 100° C., and preferably of 50° C. to 80° C.

The temperature applied upon crystallization of the hydrochloride of the pyrimidine compound (1) is not particularly limited. Crystallization may be generally carried out in the range of 5° C. to 40° C., and it is preferably 10° C. to 35° C., more preferably 10° C. to 30° C., and particularly preferably 15° C. to 25° C. When the temperature applied when the hydrochloride of the pyrimidine compound (1) is dissolved in a solvent is significantly different from the temperature applied upon crystallization, the reaction solution may be slowly cooled, as appropriate, over approximately 1 to 10 hours, depending on the temperature difference.

The time required for crystallization is not particularly limited. It is generally 1 hour or more, preferably 6 to 24 hours, and more preferably 8 to 16 hours.

The precipitated crystal of the pyrimidine compound (1) hydrochloride may be isolated by a method which is commonly applied in the present technical field, such as filtration, and further, the isolated crystal may be dried, as necessary, by a method commonly applied in the present technical field. The drying means is not particularly limited, and examples of the drying means include heating and/or drying under reduced pressure conditions. The drying temperature is preferably 50° C. or lower, and more preferably from 40° C. to 50° C. The drying time is preferably from 1 to 24 hours, and more preferably from 6 to 12 hours.

It is to be noted that Step 2 may also be carried out in the presence of the crystal (seed crystal) of pyrimidine compound (1) hydrochloride, which has been produced, separately. In this case, isopropyl acetate may be used as a solvent, instead of the aforementioned solvent. The amount of the seed crystal is not particularly limited. The seed crystal may be used in an amount of 0.00001 to 0.05 parts by mass, and preferably 0.0001 to 0.01 parts by mass, with respect to the hydrochloride of the pyrimidine compound (1).

It is preferable to add the seed crystal after the hydrochloride of the pyrimidine compound (1) has been dissolved in a solvent.

Moreover, when the crystal of the pyrimidine compound (1) hydrochloride of the present invention is produced, from the viewpoint of simplification of the production processes, Step 1 and Step 2 are continuously carried out without isolating the hydrochloride of the pyrimidine compound (1), so that a crystal of hydrochloride can be produced from the free form of the pyrimidine compound (1) in the presence of a solvent. In this case, isopropyl acetate is preferably used as a solvent.

Furthermore, it is also possible to carry out Step 2, while omitting the time required for formation of a salt in Step 1. That is to say, it is also possible that the free form of the pyrimidine compound (1) is dissolved in a solvent, that hydrogen chloride is then supplied to the obtained solution, and that the mixed solution is subjected to heating or the like, and then to cooling or the like, so as to carry out crystallization.

Other operations, etc. performed in individual steps are the same as those described above.

The pyrimidine compound (1) has an action to inhibit CETP, an action to reduce the amount of a PCSK9 protein, etc. Accordingly, the hydrochloride of the pyrimidine compound (1) of the present invention and the crystal thereof can be used as components of medicinal drugs useful for preventing and/or treating diseases such as dyslipidemia, hyper-LDL cholesterolemia and hypo-HDL-cholesterolemia.

As is apparent from Test Example 2 as described later, the crystal of the pyrimidine compound (1) hydrochloride of the present invention has excellent heat stability and can be particularly preferably used as a stable component of pharmaceutical composition.

Moreover, since the crystal of the pyrimidine compound (1) hydrochloride of the present invention has excellent heat stability, it also has high stability when it is preserved as a raw material. Thus, the crystal of the pyrimidine compound (1) hydrochloride of the present invention can be preferably used as a raw material for the production of a pharmaceutical composition. When the crystal of the pyrimidine compound (1) hydrochloride is used as such a raw material, it is not necessarily required that a crystalline form is maintained in the produced pharmaceutical composition.

When a medicinal drug comprising the hydrochloride of the pyrimidine compound (1) of the present invention or a crystal thereof is produced, the hydrochloride of the pyrimidine compound (1) or the crystal may be used singly. However, the medicinal drug may be preferably produced in the form of a pharmaceutical composition for oral administration or parenteral administration. Specific examples of the dosage form of the pharmaceutical composition for oral administration include a tablet, a capsule, a granule, a powder, a liquid and a solution for oral administration, a syrup, and a jelly for oral administration. On the other hand, specific examples of the dosage form of the pharmaceutical composition for parenteral administration include an injection, an inhalation, an ophthalmic preparation, an ear preparation, a nasal preparation, a suppository, a solid dosage form for cutaneous application, a liquid and a solution for cutaneous application, a spray, an ointment, a cream, a gel, and a patch.

These pharmaceutical compositions can be produced by adding a pharmaceutically acceptable carrier (additive). Examples of such an additive include an excipient, a binder, an extender, a disintegrator, a surfactant, a lubricant, a dispersing agent, a buffer agent, a preservative, a corrigent, a flavor, a coating agent, and a diluent, but the examples are not limited thereto.

The applied dose of the pyrimidine compound (1) is different depending on the body weight, age, sex and symptoms of a patient, etc. In general, in the case of an adult patient, approximately 0.01 to 1,000 mg of the pyrimidine compound (1) in terms of the free form thereof can be administered to the patient in one to four divided doses per day. Preferably, approximately 0.1 to 100 mg of the pyrimidine compound (1) in terms of the free form thereof can be administered to the patient in one to four divided doses per day.

EXAMPLES

Hereinafter, the present invention will be more specifically described in the following examples, test examples, and the like. However, these examples are not intended to limit the scope of the present invention. In the following examples, test examples and the like, the free form of (S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid (the free form of a pyrimidine compound (1)) can be produced by the method described in Patent Literature 2.

It is to be noted that abbreviations used in the below-mentioned examples have the following meanings.
s: singlet
d: doublet
t: triplet
q: quartet
m: multiplet
br: broad
J: coupling constant
Hz: Hertz
DMSO-$d_6$: deuterated dimethyl sulfoxide
$^1$H-NMR: proton nuclear magnetic resonance Test Example 1

Studies Regarding Crystallization Conditions

Conditions for crystallization of various types of samples (the free form of the pyrimidine compound (1), and the salts thereof (a hydrochloride, a hydrobromate, a sulfate, a D-(−)-arginine salt, and a cinchonidine salt)), were studied according to the following method.

The hydrochloride of the pyrimidine compound (1) was obtained by the method described in Step 1 in 1-1 of Example 1. Other salts were obtained by mixing, at an equimolar ratio, the free form of the pyrimidine compound (1) dissolved in methanol with an acid or a base dissolved in water, then stirring the mixture, and then distilling away the solvents.

Various types of samples were each dissolved in Solvent 1 which was in an amount 4 to 100 times (V/W) of each sample. Solvent 2 was added to the obtained solution until the solution has begun to become clouded, and predetermined operations were then performed. Thereafter, the state of the solution was observed by visual inspection, and the presence or absence of formation of a crystal was evaluated.

The results regarding the free form of the pyrimidine compound (1) are shown in Table 1, the results regarding the hydrochloride are shown in Table 2, the results regarding the hydrobromate are shown in Table 3, the results regarding the sulfate are shown in Table 4, the results regarding the D-(−)-arginine salt are shown in Table 5, and the results regarding the cinchonidine salt are shown in Table 6.

TABLE 1

Studies regarding crystallization of free form of pyrimidine compound (1)

| Solvent 1 | Solvent 2 | Operations | Observation results |
|---|---|---|---|
| 2-Propanol | Water | Hermetically sealed and left to stand at room temperature for 72 hours | Oil |
| Acetone | Water | Hermetically sealed and left to stand at room temperature for 72 hours | Separated into two layers |
| Dichloromethane | Heptane | Left to stand at room temperature for 72 hours | Oil |
| Ethanol | Heptane | Left to stand at room temperature for 72 hours | Oil |
| 2-Propanol | Heptane | Left to stand at room temperature for 72 hours | Oil |
| Ethyl acetate | Heptane | Left to stand at room temperature for 72 hours | Oil |
| Methyl ethyl ketone | Heptane | Left to stand at room temperature for 72 hours | Oil |
| Toluene | Heptane | Left to stand at room temperature for 72 hours | Oil |

TABLE 2

Studies regarding crystallization of hydrochloride of pyrimidine compound (1)

| Solvent 1 | Solvent 2 | Operations | Observation results |
|---|---|---|---|
| Ethanol | Toluene | Hermetically sealed and left to stand at room temperature for 96 hours | Homogeneous solution |
| Ethanol | Water | Hermetically sealed and left to stand at room temperature for 96 hours | Separated into two layers |
| 2-Propanol | Heptane | Hermetically sealed and left to stand at room temperature for 96 hours | Crystal precipitated |
| Methyl ethyl ketone | Heptane | Hermetically sealed and left to stand at room temperature for 96 hours | Crystal precipitated |
| Dichloromethane | Heptane | Hermetically sealed and left to stand at room temperature for 96 hours | Oil |
| Tetrahydrofuran | Toluene | Left to stand at room temperature for 96 hours | Oil |
| 1,4-Dioxane | tert-Butyl methyl ether | Left to stand at room temperature for 72 hours | Oil |
| Dichloromethane | tert-Butyl methyl ether | Left to stand at room temperature for 72 hours | Oil |

TABLE 3

Studies regarding crystallization of hydrobromate of pyrimidine compound (1)

| Solvent 1 | Solvent 2 | Operations | Observation results |
|---|---|---|---|
| 2-Propanol | Toluene | Left to stand at room temperature for 96 hours | Oil |
| Ethyl acetate | Toluene | Left to stand at room temperature for 96 hours | Oil |
| 2-Propanol | Heptane | Left to stand at room temperature for 72 hours | Oil |
| 1,4-Dioxane | Heptane | Left to stand at room temperature for 72 hours | Oil |
| Methyl ethyl ketone | Heptane | Left to stand at room temperature for 72 hours | Oil |
| Dichloromethane | tert-Butyl methyl ether | Left to stand at room temperature for 72 hours | Oil |
| 1,4-Dioxane | tert-Butyl methyl ether | Left to stand at room temperature for 72 hours | Oil |
| Acetone | tert-Butyl methyl ether | Left to stand at room temperature for 72 hours | Oil |

TABLE 4

Studies regarding crystallization of sulfate of pyrimidine compound (1)

| Solvent 1 | Solvent 2 | Operations | Observation results |
|---|---|---|---|
| 2-Propanol | Toluene | Left to stand at room temperature for 96 hours | Oil |
| Tetrahydrofuran | Toluene | Left to stand at room temperature for 96 hours | Oil |
| 2-Propanol | Heptane | Left to stand at room temperature for 96 hours | Oil |
| Methyl ethyl ketone | Heptane | Left to stand at room temperature for 72 hours | Oil |
| Ethyl acetate | Heptane | Left to stand at room temperature for 72 hours | Oil |
| 1,4-Dioxane | Heptane | Left to stand at room temperature for 72 hours | Oil |
| 2-Propanol | tert-Butyl methyl ether | Left to stand at room temperature for 72 hours | Oil |
| Acetonitrile | tert-Butyl methyl ether | Left to stand at room temperature for 72 hours | Oil |

TABLE 5

Studies regarding crystallization of D-(−)-arginine salt of pyrimidine compound (1)

| Solvent 1 | Solvent 2 | Operations | Observation results |
|---|---|---|---|
| Methanol | Water | Left to stand at room temperature for 2 days | Gelatinous substance |
| Ethanol | Toluene | Left to stand at room temperature for 2 days | Homogeneous solution |
| Ethanol | Heptane | Left to stand at room temperature for 2 days | Homogeneous solution |
| Acetonitrile | tert-Butyl methyl ether | Left to stand at room temperature for 2 days | Oil |
| Ethyl acetate | Toluene | Left to stand at room temperature for 2 days | Oil |
| Ethyl acetate | Heptane | Left to stand at room temperature for 2 days | Oil |
| Tetrahydrofuran | Water | Left to stand at room temperature for 2 days | Oil |
| Tetrahydrofuran | Heptane | Left to stand at room temperature for 2 days | Oil |

TABLE 6

Studies regarding crystallization of cinchonidine salt of pyrimidine compound (1)

| Solvent 1 | Solvent 2 | Operations | Observation results |
|---|---|---|---|
| Methanol | — | Left to stand at room temperature for 2 days | Homogeneous solution |
| Ethanol | — | Left to stand at room temperature for 2 days | Homogeneous solution |
| 2-Propanol | — | Left to stand at room temperature for 2 days | Homogeneous solution |
| Tetrahydrofuran | — | Left to stand at room temperature for 2 days | Homogeneous solution |
| Chloroform | — | Left to stand at room temperature for 2 days | Homogeneous solution |
| Ethyl acetate | — | Left to stand at room temperature for 2 days | Homogeneous solution |
| Acetone | — | Left to stand at room temperature for 2 days | Homogeneous solution |
| tert-Butyl methyl ether | — | Left to stand at room temperature for 2 days | Homogeneous solution |

From the above study results, it became clear that a crystal is specifically precipitated from the pyrimidine compound (1), when the pyrimidine compound (1) is converted to a hydrochloride.

Example 1

Production of Crystal of (S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid hydrochloride 1-1: Production of Crystal of Pyrimidine Compound (1) Hydrochloride, Part 1

Step 1

1.1 kg (1.35 mol) of a free form of (S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid was dissolved in tert-butyl methyl ether (15.3 kg) under an argon atmosphere, and the obtained solution was then cooled to 0° C. Subsequently, 503.9 g of a 16.7% hydrogen chloride/1,4-dioxane solution (hydrogen chloride: 2.31 mol) was added dropwise to the obtained solution at a temperature of 0° C. to 10° C., and the obtained mixture was then stirred at the same temperature as described above for 1 hour. Thereafter, the precipitated solid was collected by filtration, and was then washed with cooled tert-butyl methyl ether (1.85 kg). The resultant was dried under reduced pressure at a temperature of 40° C. to 50° C. for 12 hours, so as to afford 1.14 kg of an amorphous substance of the (S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid hydrochloride (yield: 100%).

¹H-NMR (400 MHz, DMSO-d₆) δ: 0.72-0.92 (7H, m), 1.30 (1H, m), 1.50 (3H, d, J=6.6 Hz), 1.62-1.70 (5H, m), 2.02 (2H, d, J=6.8 Hz), 2.71 (1H, m), 2.75 (1H, brs), 2.90 (3H, brs), 3.07 (3H, s), 3.62 (2H, t, J=5.5 Hz), 4.40 (2H, t, J=5.7 Hz), 4.67 (1H, d, J=17.6 Hz), 4.80 (1H, d, J=17.8 Hz), 6.24 (1H, q, J=6.8 Hz), 7.10 (1H, s), 7.33 (1H, brs), 7.47 (1H, d, J=8.3 Hz), 7.84 (2H, s), 7.94 (1H, s), 8.35 (2H, s).

Step 2

The amorphous substance (676 mg) of the (S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid hydrochloride obtained in Step 1 was dissolved in 2-propanol (1.35 mL) by heating it at a temperature of 50° C. to 55° C. Thereafter, heptane (676 μL) was added to the obtained solution at 50° C., and the obtained mixture was hermetically sealed and was left to stand at a temperature of 5° C. to 15° C. for 14 hours. Thereafter, the precipitated solid was collected by filtration, and was then dried under reduced pressure at 40° C. to afford 576 mg of a crystal of the (S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid hydrochloride (yield: 85%).

1-2: Production of Crystal of Pyrimidine Compound (1) Hydrochloride, Part 2

1.14 kg (1.35 mol) of the amorphous substance of the (S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid hydrochloride obtained by the method described in Step 1 of 1-1 above was suspended in isopropyl acetate (9.98 kg), followed by heating it to a temperature of 65° C. to 75° C., so that the amorphous substance was dissolved therein. Thereafter, 11 g of the crystal of the (S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid hydrochloride obtained by the method described in Step 2 of 1-1 above was added as a seed crystal to the obtained solution and the obtained mixture was then stirred for 3 hours at the same temperature as described above. Thereafter, the reaction mixture was cooled to a temperature of 45° C. to 55° C. over 2 hours, and was then cooled to a temperature of 15° C. to 25° C. over 3 hours, and the resultant was further stirred for 16 hours at the same temperature as described above. After that, the precipitated crystal was collected by filtration, and was then washed with isopropyl acetate (1,720 g). Thereafter, the resulting crystal was dried under reduced pressure at a temperature of 35° C. to 45° C. for 12 hours to afford 1.02 kg of a crystal of the (S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid hydrochloride (yield: 85%).

As a result of the elemental analysis, it became clear that the obtained hydrochloride was a monohydrochloride, as described below.

Elemental analysis results:

Calculated (as a monohydrochloride): C: 50.91%, H: 4.98%, N: 6.60%, and Cl: 4.17%.

Found: C: 50.79%, H: 4.70%, N: 6.40%, and Cl: 3.94%.

¹H-NMR (400 MHz, DMSO-d₆) δ: 0.72-0.92 (7H, m), 1.29 (1H, m), 1.49 (3H, d, J=6.8 Hz), 1.62-1.70 (5H, m), 2.02 (2H, d, J=6.6 Hz), 2.71 (1H, m), 2.80-2.90 (3H, m), 3.07 (3H, s), 3.62 (2H, t, J=5.5 Hz), 4.40 (2H, t, J=5.7 Hz), 4.65 (1H, d, J=16.4 Hz), 4.78 (1H, d, J=17.1 Hz), 6.23 (1H, q, J=6.8 Hz), 7.09 (1H, s), 7.29 (1H, d, J=8.0 Hz), 7.45 (1H, d, J=7.8 Hz), 7.83 (2H, s), 7.94 (1H, s), 8.35 (2H, s).

1-3: Production of Crystal of Pyrimidine Compound (1) Hydrochloride, Part 3

16.1 kg (19.8 mol) of a free form of the (S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid was dissolved in isopropyl acetate (124 kg) under an argon atmosphere. The obtained solution was heated to a temperature of 40° C. to 50° C. Subsequently, 15.0 kg of a 6.3% hydrogen chloride/isopropyl acetate solution (hydrogen chloride: 25.98 mol) was added dropwise to the obtained solution, and the obtained mixture was then heated to a temperature of 65° C. to 75° C. 25 g of the crystal of the (S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid hydrochloride obtained by the method described in Step 2 of 1-1 above was added as a seed crystal to the obtained solution, and 7.0 kg of a 6.3% hydrogen chloride/isopropyl acetate solution (hydrogen chloride: 12.08 mol) was further added dropwise to the mixed solution, and the obtained mixture was then stirred for 7 hours at the same temperature as described above. Thereafter, the reaction solution was cooled to a temperature of 45° C. to 55° C. over 3 hours, and was then cooled to a temperature of 15° C. to 25° C. over 4 hours, and the resultant was further stirred at the same temperature as described above for 16 hours. Thereafter, the precipitated crystal was collected by filtration, and was then washed with isopropyl acetate (32.4 kg). The resultant was dried under reduced pressure at a temperature of 40° C. to 50° C. for 12 hours to afford 15.35 kg of a crystal of the (S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid hydrochloride (yield: 91%).

As a result of the elemental analysis, it became clear that the obtained hydrochloride was a monohydrochloride.

Elemental analysis results:

Calculated (as a monohydrochloride): C: 50.91%, H: 4.98%, N: 6.60%, and Cl: 4.17%.

Found: C: 50.82%, H: 4.98%, N: 6.56%, and Cl: 4.15%.

¹H-NMR (400 MHz, DMSO-d₆) δ: 0.72-0.92 (7H, m), 1.29 (1H, m), 1.49 (3H, d, J=6.8 Hz), 1.62-1.70 (5H, m), 2.02 (2H, d, J=6.6 Hz), 2.71 (1H, m), 2.80-2.90 (3H, m), 3.07 (3H, s), 3.62 (2H, t, J=5.5 Hz), 4.40 (2H, t, J=5.7 Hz), 4.65 (1H, d, J=16.4 Hz), 4.78 (1H, d, J=17.1 Hz), 6.23 (1H, q, J=6.8 Hz), 7.09 (1H, s), 7.29 (1H, d, J=8.0 Hz), 7.45 (1H, d, J=7.8 Hz), 7.83 (2H, s), 7.94 (1H, s), 8.35 (2H, s).

1-4: Evaluation of Physical Properties of Crystal of Pyrimidine Compound (1)

The crystal obtained in 1-3 above was subjected to a powder X-ray diffraction measurement and a thermal analysis measurement, as described below.

<Powder X-Ray Diffraction Measurement>

The crystal obtained in 1-3 above was subjected to a powder X-ray diffraction measurement. The crushed crystal sample was mounted on a sample holder portion of a silicon reflection-free sample plate for X-ray diffraction, and the powder X-ray diffraction measurement was then carried out under the following conditions.

Powder X-ray diffraction measurement apparatus: RINT-UltimaIV-Protectus (manufactured by Rigaku Corporation)
  Type of X-ray: copper Kα X rays (λ=1.54 Å)
  Scanning field of diffraction angle 2θ: 3.00° to 40.00°
  Sampling width: 0.02°
  Scanning rate: 2.00°/min The obtained diffraction pattern is shown in FIG. 1. In FIG. 1, the longitudinal axis indicates diffraction intensity (count/sec (cps)), and the horizontal axis indicates diffraction angle 2θ (°).

With regard to major peaks having a relative intensity of 30 or more, the diffraction angle 2θ, full width at half maximum, d value, intensity, and relative intensity of the peaks are shown in Table 7.

From FIG. 1 and Table 7, it became clear that major peaks are found at diffraction angles (2θ) around 14.0±0.2°, around 18.3±0.2°, around 20.1±0.2°, around 20.5±0.2°, around 21.3±0.2°, around 21.8±0.2°, around 23.3±0.2°, and around 24.0±0.2°.

Moreover, it also became clear that peaks with strong intensity are found at diffraction angles (2θ) around 18.3±0.2° and around 20.5±0.2°, and in particular, around 20.5±0.2°.

TABLE 7

| Peak No. | 2θ | Full width at half maximum | d value | Intensity | Relative intensity |
| --- | --- | --- | --- | --- | --- |
| 1 | 14.000 | 0.235 | 6.3205 | 1232 | 31 |
| 2 | 18.260 | 0.235 | 4.8545 | 2486 | 62 |
| 3 | 20.100 | 0.235 | 4.4140 | 1279 | 32 |
| 4 | 20.500 | 0.235 | 4.3288 | 4040 | 100 |
| 5 | 21.340 | 0.235 | 4.1603 | 1194 | 30 |
| 6 | 21.780 | 0.235 | 4.0772 | 1386 | 35 |
| 7 | 23.320 | 0.235 | 3.8113 | 1415 | 36 |
| 8 | 23.960 | 0.212 | 3.7109 | 1421 | 36 |

<Thermal Analysis Measurement>

The crystal obtained in Example 1-3 was subjected to a thermal analysis measurement. Approximately 5 mg of a sample was precisely weighed in an aluminum pan for thermal analysis, and $Al_2O_3$ was used as a reference substance. The thermal analysis was carried out under a nitrogen atmosphere (150 mL/min) at a temperature increase rate of 10° C./min by a differential thermal analysis method (DTA) and a thermogravimetry method (TG), using a thermal analysis apparatus Thermo Plus 2 System (manufactured by Rigaku Corporation).

The results of the thermal analysis measurement are shown in FIG. 2. In FIG. 2, the longitudinal axis indicates the thermal electromotive force (μV) of thermocouple with respect to a DTA curve, and also indicates mass change (mg) with respect to a TG curve. The horizontal axis indicates temperature (° C.).

As shown in FIG. 2, the crystal of the pyrimidine compound (1) hydrochloride had an endothermic peak around 162±5° C. (which is specifically 161.6° C.) in the differential thermal analysis (DTA). From the aforementioned thermal analysis measurement results, it was considered that the crystal of the pyrimidine compound (1) hydrochloride has a melting point around approximately 162±5° C.

Test Example 2

Heat Stability Test

A test compound was placed in a glass bottle, and it was then preserved for a predetermined period of time under temperature conditions of 80° C., 100° C., or 120° C. Thereafter, the remaining percentage (%) of the pyrimidine compound (1) in the test compound was measured.

The remaining percentage was obtained by measuring the rate of the pyrimidine compound (1) contained in the test compound according to high performance liquid chromatography and expressing the measured value as a peak area percentage. In the measurement according to high performance liquid chromatography, an ODS column was used as a column, and a mixture of two solvents, namely, a 0.1% TFA aqueous solution and a 0.1% TFA acetonitrile solution, was used as a solvent. The detection wavelength was set at 242 nm.

From the obtained area percentage of the pyrimidine compound (1), the remaining percentage was calculated according to the following calculation formula.

Remaining percentage (%)=Area percentage of pyrimidine compound (1) after preservation/area percentage of pyrimidine compound (1) before preservation×100  [Expression 1]

As test compounds, the crystal obtained in Example 1-3 (a crystal of the pyrimidine compound (1) hydrochloride) and a free form of the pyrimidine compound (1) were used.

The results are shown in Table 8.

TABLE 8

| | Remaining percentage (%) | | |
| --- | --- | --- | --- |
| | After preservation at 80° C. for 72 hours | After preservation at 100° C. for 24 hours | After preservation at 120° C. for 16 hours |
| Crystal of pyrimidine compound (1) hydrochloride | 100.0 | 100.0 | 99.5 |
| Free form of pyrimidine compound (1) | 99.5 | 89.3 | 71.5 |

From the test results shown in Table 8, it became clear that the crystal of the pyrimidine compound (1) hydrochloride has excellent heat stability.

INDUSTRIAL APPLICABILITY

According to the present invention, the pyrimidine compound (1) useful for preventing and/or treating diseases such as dyslipidemia can be provided in a form, which is highly pure and homogeneous, and is suitable for production of pharmaceutical products with high quality, and thus, it can be utilized, for example, in the industry of pharmaceutical products.

The invention claimed is:

1. A crystal of (S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid hydrochloride, wherein the powder X-ray diffraction pattern obtained by irradiation with copper Kα X rays has a peak(s) at one or more diffraction angles (2θ) selected from the group consisting of around 14.0±0.2°, around 18.3±0.2°, around 20.1±0.2°, around 20.5±0.2°, around 21.3±0.2°, around 21.8±0.2°, around 23.3±0.2°, and around 24.0±0.2°.

2. The crystal according to claim 1, wherein the hydrochloride is a monohydrochloride.

3. A pharmaceutical composition comprising the crystal according to claim 1 and a pharmaceutically acceptable carrier.

4. A method for producing a pharmaceutical composition, comprising mixing the crystal according to claim 1 with a pharmaceutically acceptable carrier.

\* \* \* \* \*